United States Patent
Carl

(10) Patent No.: US 8,579,903 B2
(45) Date of Patent: Nov. 12, 2013

(54) DEVICES AND METHODS FOR STABILIZING A SPINAL REGION

(75) Inventor: Allen Carl, Slingerlands, NY (US)

(73) Assignee: K2M, Inc., Leesburg, VA (US)

( * ) Notice: Subject to any disclaimer, the term of this patent is extended or adjusted under 35 U.S.C. 154(b) by 988 days.

(21) Appl. No.: 12/309,254

(22) PCT Filed: Jul. 13, 2007

(86) PCT No.: PCT/US2007/016044
§ 371 (c)(1),
(2), (4) Date: Dec. 30, 2009

(87) PCT Pub. No.: WO2008/008522
PCT Pub. Date: Jan. 17, 2008

(65) Prior Publication Data
US 2010/0114098 A1    May 6, 2010

Related U.S. Application Data

(60) Provisional application No. 60/830,516, filed on Jul. 13, 2006.

(51) Int. Cl.
*A61F 2/46* (2006.01)
*A61B 17/80* (2006.01)
*A61B 17/58* (2006.01)

(52) U.S. Cl.
USPC .......................... 606/86 R; 606/279; 606/96

(58) Field of Classification Search
USPC ....... 606/79–85, 86 R, 86 A, 96–97, 99, 279; 623/17.11–17.16
See application file for complete search history.

(56) References Cited

U.S. PATENT DOCUMENTS

| | | |
|---|---|---|
| 3,426,364 A | 2/1969 | Lumb |
| 4,059,115 A | 11/1977 | Jumashev et al. |
| 4,135,506 A | 1/1979 | Ulrich |
| 4,335,715 A | 6/1982 | Kirkley |
| 4,773,402 A | 9/1988 | Asher et al. |
| 4,790,303 A | 12/1988 | Steffee |
| 4,834,757 A | 5/1989 | Brantigan |
| 4,907,577 A | 3/1990 | Wu |
| 4,941,466 A | 7/1990 | Romano |
| 5,352,224 A | 10/1994 | Westermann |
| 5,355,588 A | 10/1994 | Brandenburg, Jr. et al. |
| 5,415,661 A | 5/1995 | Holmes |
| 5,423,826 A | 6/1995 | Coates et al. |
| 5,425,772 A | 6/1995 | Brantigan |
| 5,445,639 A | 8/1995 | Kuslich et al. |
| 5,509,918 A | 4/1996 | Romano |
| 5,527,316 A | 6/1996 | Stone et al. |
| 5,545,164 A | 8/1996 | Howland |
| 5,591,165 A | 1/1997 | Jackson |
| 5,591,235 A | 1/1997 | Kuslich |
| 5,700,265 A | 12/1997 | Romano |

(Continued)

*Primary Examiner* — Matthew Lawson
(74) *Attorney, Agent, or Firm* — Edwards Wildman Palmer LLP

(57) ABSTRACT

Apparatuses and methods deliver implants through a posterior aspect of a vertebral body such as a pedicle and place the implant or perform a procedure into the anterior aspect of the vertebral body. A representative apparatus includes an outer cannula, an advancer tube and a drill assembly. It is envisioned that at least one of the outer cannula, the advancer tube or the drill assembly can be viewed in vivo using for example, a CT scan or fluoroscope. Also included is an apparatus for forming an arcuate channel in bone material. The apparatus includes an advancer tube and a drill assembly.

13 Claims, 17 Drawing Sheets

(56) References Cited

U.S. PATENT DOCUMENTS

| | | |
|---|---|---|
| 5,765,289 A | 6/1998 | Schulz et al. |
| D401,335 S | 11/1998 | Koros et al. |
| 5,895,183 A | 4/1999 | McDaniel et al. |
| 5,899,908 A | 5/1999 | Kuslich et al. |
| 5,928,267 A | 7/1999 | Bonutti et al. |
| 5,974,674 A | 11/1999 | Kelly |
| 6,056,749 A | 5/2000 | Kuslich |
| 6,241,769 B1 | 6/2001 | Nicholson et al. |
| RE37,479 E | 12/2001 | Kuslich |
| 6,342,056 B1 | 1/2002 | Mac-Thiong et al. |
| 6,425,919 B1 | 7/2002 | Lambrecht |
| 6,558,390 B2 | 5/2003 | Cragg |
| 6,575,979 B1 | 6/2003 | Cragg |
| 6,592,559 B1 | 7/2003 | Pakter et al. |
| 6,607,530 B1 | 8/2003 | Carl et al. |
| 6,805,697 B1 | 10/2004 | Helm et al. |
| 6,923,811 B1 | 8/2005 | Carl et al. |
| 2004/0059333 A1* | 3/2004 | Carl et al. ............. 606/61 |
| 2004/0092933 A1* | 5/2004 | Shaolian et al. ............. 606/61 |
| 2004/0158325 A1 | 8/2004 | Errico et al. |
| 2005/0177168 A1 | 8/2005 | Brunnett et al. |
| 2005/0203624 A1 | 9/2005 | Serhan et al. |
| 2005/0267481 A1 | 12/2005 | Carl et al. |
| 2007/0027545 A1* | 2/2007 | Carls et al. ............. 623/17.12 |

\* cited by examiner

DEVICES AND METHODS FOR STABILIZING A SPINAL REGION

This application is a National Stage Filing of PCT Application No. PCT/US2007/016044, filed Jul. 13, 2007, which application claims the benefit of U.S. Provisional Application Ser. No. 60/830,516 filed Jul. 13, 2006, the teachings of all being incorporated herein by reference.

BACKGROUND OF THE INVENTION

1. Field of the Invention

The present invention relates generally to devices and methods for delivering implants or performing procedures at sites within intervertebral discs or adjacent vertebral endplates, and more specifically to devices and methods for delivering implants through a posterior aspect of a vertebral body such as a pedicle or performing a procedure into the anterior aspect of the spinal column.

2. Background of the Related Art

Surgery for spine fusion or stabilization generally involves using implants and instrumentation to provide support to the affected area of the spine while allowing the bones thereof to fuse. The technology initially evolved using bone chips around and on the top of an area of the spine that had been roughened to simulate a fracture in its consistency. The area, having encountered the bone chips, would then proceed to heal like a fracture, incorporating the bone chips. However, surgical procedures dealing with the spine present notable challenges. For example, bioengineers have been required to identify the various elements of the complex motions that the spine performs, and the components of the complex forces it bears. This complexity has made it difficult to achieve adequate stability and effective healing in surgical procedures directed to the spine.

One surgical technique provided by Cloward, involves cutting a dowel type hole with a saw across or through the moveable intervertebral disc and replacing it with a bone graft that was harvested from the hip bone. This procedure results in a fusion of the adjacent vertebral bodies and limits motion and mobility. However, as a result of the complex motions of the spine, it is often difficult to secure the dowel from displacing. Further, it has become apparent over time, however, that this particular technique does not always yield a secure fusion.

Other techniques have been developed that involve the placement of various hardware elements, including rods and hooks, rods and screws and plates and screws. The dowel technique also has advanced over the past ten to fifteen years or so, with dowels being fabricated from cadaver bone or metals such as titanium or stainless steel. These techniques, whether using hardware, dowels or some combination thereof, have a common goal to enhance stability by diminishing movement, thereby resulting in or enhancing the potential of a fusion of adjacent vertebral bones. For example, in one of these other techniques, the disc is removed and adjacent vertebrae are positioned in a stable position by placing a plate against and traversing them, which plate is secured or anchored to each by means of screws. A disadvantage of such procedures is the use of components that protrude outwardly, which may contact and damage a body part, such as the aorta, the vena cava, the sympathetic nerves, the lungs, the esophagus, the intestine and the ureter. Also, many constructions involve components that may loosen and cause undesirable problems, often-necessitating further surgical intervention.

In another procedure, cages in the form of two parallel circular or rectangular devices are made out of a material such as titanium or stainless steel and these devices are fenestrated. Bone is packed in the center of the devices that will heal to adjacent bone through each fenestration. In this procedure, the disc space is distracted so all ligamentous structures are taut and the bones are held in their normal maximal position of distraction. Because the cages are implanted in spongy bone, they are more likely to collapse into the surrounding bone, thus resulting in loss of distraction and subsequently cage loosening and dislodgment.

U.S. Pat. No. 5,591,235 discloses a spinal fixation device and technique for stabilizing vertebrae. In this technique, a hollow screw is inserted into a hole, preferably a hole saw recess, in each adjoining vertebrae. A channel is cut into the vertebrae, which is lined up with corresponding axial slots in the screw. A rod is inserted into the channel and so as to pass through the axial slots in the screw. The rod is secured to each of the screws by means of a locking cap. The rod also is arranged so as to provide a bridge between the hollow screws in the adjoining vertebrae. Certain disadvantages have been surmised using such a device and technique. For example, it has become apparent that the trough in the vertebral bodies destabilizes some of the cortex of the vertebrae body wall, which is the strongest component.

In addition to fixation or fusion of vertebral columns, the prior art also describes methods or other spinal repair procedures, such as discectomy wherein an artificial disc or prosthetic device is placed within the vertebrae of the spine. For such prior art methods and related devices, there have been short comings such as having difficulty in securing and maintaining the prostheses within the vertebral space or resulting in significant modification or damage to the load bearing surfaces of the vertebrae in an effort to secure the prosthesis.

Another method or other spinal repair technique involves augmentation of the nucleus of an intervertebral disk of the spine. The intervertebral disk is a flexible cartilaginous structure that is disposed between adjacent vertebrae. These disks form joints between the bodies of the vertebrae, which serve to unite adjacent vertebrae and to permit movement between them. These disks also play a role as shock absorbers when force is transmitted along the vertebral column during standing and movement.

Each intervertebral disk is formed of two parts, a central mass called the nucleus pulpsous (herein the nucleus) and a surrounding fibrous layer, the annulus fibrosus (herein the annulus). The nucleus has a semi-gelatinous consistency, which allows it to become deformed when pressure is placed upon it, enabling the disk to change shape as the vertebral column moves and acts in a hydrostatic manner. The top and bottom of the disc are supported by relatively bony endplates.

There is described in U.S. Pat. Nos. 5,047,055; 5,824,093 6,264,695; the teachings of which are incorporated herein by reference, various techniques and/or prosthetics for use in replacing or augmenting a spinal disc nucleus. Given the structure of the disk and its location between adjacent vertebrae, it is not s simple task to access the nucleus for the insertion of such prosthetics or materials to augment the nucleus. One technique for accessing the nucleus contemplates using the defect in the annulus, however, in practice the defect usually needs to be enlarged to allow the insertion of the prosthetic. Another technique contemplates having the surgeon drill through one of the adjacent bodies using a lateral approach. This technique relies heavily on the skill and dexterity of the surgeon not to damage surrounding tissues, nerves and blood vessels. Also, the hole formed by such drilling is not easily sealed because of its shape and configuration.

Various implants, fusion devices, cages, and the like may be used to treat pathological vertebral bodies and intervertebral discs are known in the art. Certain physiological environments present challenges to precise and minimally invasive delivery. Also, the difficulty and danger of the typical implantation procedure itself, due to the proximity of the aorta (if an anterior approach is used) and the spinal cord (if a posterior approach is used), limits the size and ease of placement of the implant. In light of the inherent limitations involved with delivery of medical devices to the disc environment, safer and less invasive surgical approaches are desired.

Therefore, there is a need for an apparatus and method for delivering implants through a posterior aspect of a vertebral body such as a pedicle and placing the implant or performing a procedure into the anterior aspect of the spinal column. There is also a need for implants which do not protrude from the vertebral body and provide stable support to the spine.

SUMMARY OF THE INVENTION

The present invention is directed to apparatuses and methods for delivering implants through a posterior aspect of a vertebral body such as a pedicle and placing the implant or performing a procedure proximal to the anterior aspect of the spinal column.

Also, disclosed is an apparatus for forming an arcuate channel in one or more segments of a bone, bony structure or vertebrae of a spine. The apparatus includes an outer cannula, and advancer tube and a drill assembly. It is envisioned that at least one of the outer cannula, the advancer tube or the drill assembly can be viewed in vivo using, for example, a CT scan or other orientation imaging technology.

The outer cannula has a proximal end and a distal end and a passageway extending therebetween. Preferably, the outer cannula is rigid and made from material, such as, surgical steel.

The advancer tube is adapted and configured for being slidably received within the passageway of the outer cannula and has a central bore which extends longitudinally from a proximal end of the tube to a distal end of the tube. The advancer tube is configured to have at least one preformed arcuate segment when in an unconstrained configuration. The advancer tube is able to be constrained to a second configuration when inserted into the passageway of the outer cannula, and wherein the advancer tube returns to its unrestrained configuration when at least a portion of the tube outside the passageway of the outer cannula. In certain embodiments, it is envisioned that the constrained configuration of the advancer tube is substantially straight.

The drill assembly includes a drill bit and a drive cable. The drill bit is attached to the drive cable and operatively positioned proximate to the distal end of the advancer tube. The drive cable extends from the drill bit axially through the central bore of the advancer tube, wherein the drill bit and drive cable are rotationally movable with respect to the advancer tube. When the advancer tube is moved distally with respect to the outer cannula and at least a portion of the preformed arcuate segment of the advancer tube is in the unconstrained configuration, the drill bit moves distally and traverses an arcuate path.

In a preferred embodiment, the advancer tube is made from a shape memory alloy. In certain constructions, the advancer tube is made from a nickel-titanium alloy, such as nitinol. Alternatively, the advancer tube can be made from a metal alloy selected from the group consisting of Copper-Aluminum-Nickel, Copper-Aluminum-Zinc, Copper-Tin or Copper-Zinc. Still further, the advancer tube can be made from a plastic material.

Preferably, the preformed arcuate segment of the advancer tube defines a bend of between about 10 and about 110 degrees. In certain embodiments, the preformed arcuate segment defines a bend of between about 80 and about 100 degrees.

It is envisioned that the disclosed apparatus may further comprise a mechanism associated with the proximal end of the advancer tube for determining the plane of the at least one arcuate segment. In certain embodiment, the proximal end of the advancer tube includes visible markings which indicate the plane at which the at least one arcuate segment is located in and also provide indications as the measure of deviation from the plane.

The present invention is also directed to an apparatus for forming an arcuate channel in bone material. The apparatus includes an advancer tube and a drill assembly. The advancer tube is adapted and configured for being received within an access hole formed in a bone, bony structure or vertebrae of a spine and has a central bore which extends longitudinally from its proximal end to its distal end. The advancer tube is also configured to have at least one preformed arcuate segment when in an unconstrained configuration. The advancer tube is able to be constrained to a second configuration when inserted into the passageway formed in a bone material, and wherein the advancer tube returns to its unrestrained configuration when at least a portion of the tube is positioned outside the passageway formed in a bone, bony structure or vertebrae of a spine.

The drill assembly includes a drill bit and a drive cable, the drill bit being attached to the drive cable. In a preferred embodiment, the drill bit is positioned proximate to the distal end of the advancer tube and the drive cable extends from the drill bit axially through the central bore of the advancer tube. The drill bit and drive cable are rotationally movable with respect to the advancer tube and when the advancer tube is moved distally with respect to the passageway formed in the bone material and at least a portion of the preformed arcuate segment of the advancer tube is in the unconstrained configuration, the drill bit moves distally and traverses an arcuate path.

The present application is also directed to a method for treating the spinal region of a patient after open surgery is performed to expose a portion of the patient's spine. In the disclosed method an access hole is drilled into the patient's vertebrae which extends from a pedicle into the marrow of a vertebral body to a first depth. Then a cannula is inserted into the access hole, the cannula having a proximal end and a distal end and a passageway extending therebetween. An advancer tube is then slidably inserted into the passageway of the outer cannula. Preferably, the advancer tube has a central bore extending longitudinally from its proximal end to its distal end and includes at least one preformed arcuate segment when in an unconstrained configuration. Moreover, the advancer tube is able to be constrained to a second configuration when inserted into the passageway of the cannula, and wherein the advancer tube returns to its unrestrained configuration when at least a portion of the tube is outside the passageway of the cannula.

The disclosed method also includes the step of inserting a drill assembly into the central bore of the advancer tube. It is envisioned that the drill assembly includes a drill bit and a drive cable, the drill bit being attached to the drive cable and operatively positioned proximate to the distal end of the advancer tube. In a preferred embodiment, the drive cable extends from the drill bit axially through the central bore of the advancer tube and the drill bit and drive cable are rotationally movable with respect to the advancer tube. Then the advancer tube and drill bit and slide distally with respect to the cannula to a second depth such that at least a portion of the tube is in the unconstrained configuration and the drill bit moves distally in arcuate path through an endplate of the vertebral body into the intervertebral disc.

The present application is also directed to an apparatus for forming an arcuate channel in one or more segments of a bone, bony structure or vertebrae of a spine which includes an outer cannula, an advancer tube and a medical implement, such as for example, forceps or a drill assembly. The outer cannula and advancer tube used in the disclosed apparatus are similar to those previously described.

The medical device is adapted and configured for being inserted into the central bore of the advancer tube such that when a least a portion of the preformed arcuate segment of the advancer tube is in the unconstrained configuration and projecting past the distal end of the outer cannula, a portion of the medical implement is guided in an arcuate path by the advancer tube.

The present application is also directed to a method of treating the spinal region of a patient. The disclosed method includes the steps of creating a first access hole through a pedicle of a vertebral body and advancing an instrument through the hole and within the vertebral body to a location adjacent a vertebral endplate. Then a second hole is created through the vertebral endplate, the instrument is advanced through the second hole and within an intervertebral disc; and a procedure is performed.

It is envisioned that the adjacent endplate is a superior endplate or an inferior endplate. Still further, the access holes can be created through drilling, pile driving or boring. However, it is also envisioned that the access holes can be created through punching or piercing. Moreover, the access holes can be created through chemical breakdown, ultrasound, $H_2O$ cutting or by dissolving the bone.

In certain embodiments, the location adjacent a vertebral endplate is proximal to an anterior portion of the vertebral body. In other embodiments, the location adjacent a vertebral endplate is proximal to a medial of the vertebral body. It is also envisioned that the second access hole can be formed through cancellous bone. Alternatively, the second access hole can be formed through cortical bone.

In certain embodiments of the present method, the procedure comprises a fusion. It is envisioned that the procedure can include delivering harvested bone and/or delivering an expansion device operable to increase or selectively adjust the distance between adjacent endplates. In representative methods the procedure can include at least a partial discectomy and/or preparing an implant delivery site.

It is also envisioned that the disclosed method can include the steps of engaging the adjacent vertebral body endplate; advancing through said second access hole an expansion member; expanding the expansion member through an intervertebral space; and contacting and displacing a second vertebral endplate thereby increasing the intervertebral space.

In certain embodiments, the access holes are created through the destruction of tissue using techniques such as, for example, heating, ablating, cooling, or electrifying. It is presently envisioned that the procedure could include joint motion preservation, disc repair or disc replacement.

The present disclosure is also directed to a method of treating the spinal region of a patient which includes the steps of accessing a posterior aspect of a vertebral body; advancing an implant delivery device transversely through said body; advancing said device vertically through an adjacent endplate of said vertebral body and into an intervertebral disc; and delivering the implant.

Certain preferred embodiments of the disclosed method include the step of preparing the intervertebral disc and adjacent endplate to accept the delivery of said implant. Moreover, the method may include advancing an implant delivery device transversely through a pedicle of a vertebral body. The implant is for example, a fusion cage.

In a representative method the delivery device includes a sleeve and a advanceable arcuate probe having boring mechanism at its distal end and the implant is at least a partial disc replacement.

These and other aspects of the apparatuses and methods of the subject invention will become more readily apparent to those having ordinary skill in the art from the following detailed description of the invention taken in conjunction with the figures and appended material.

DETAILED DESCRIPTION OF THE PREFERRED EMBODIMENT

Reference is now made to the accompanying figures for the purpose of describing, in detail, preferred and exemplary embodiments of the present disclosure. The figures and detailed description are provided to describe and illustrate examples in which the disclosed subject matter may be made and used, and are not intended to limit the scope thereof.

Figure 1A:
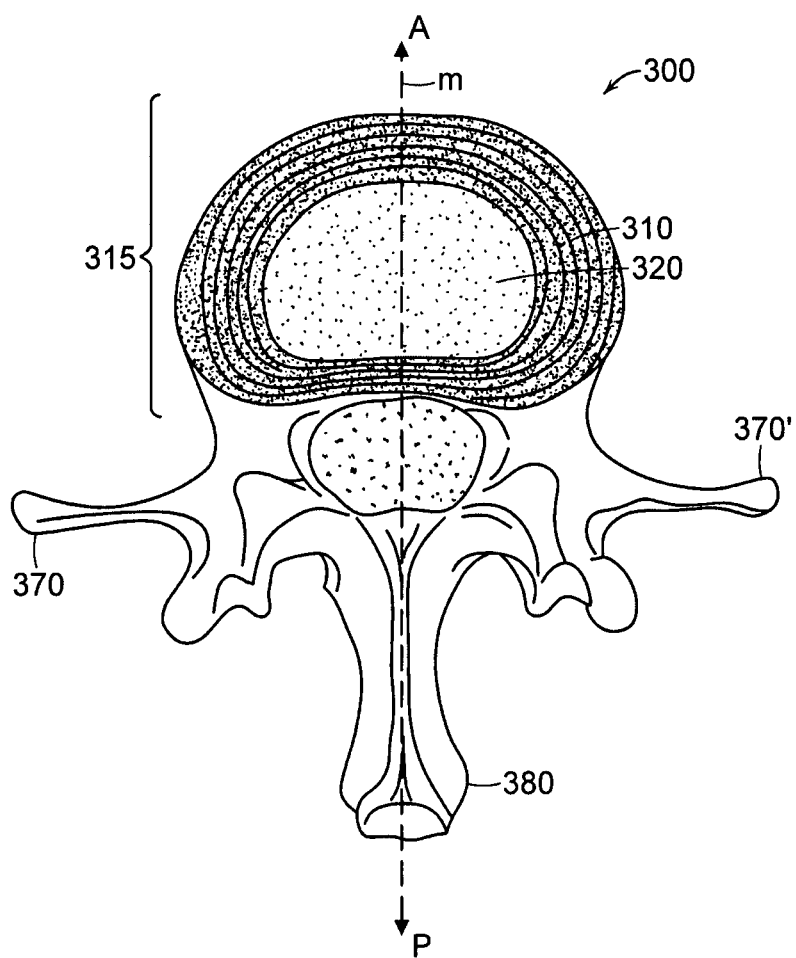
FIG. 1A provides a cross-sectional view taken horizontally through the axis of a spine and illustrating a disc structure.
Figure 1B:
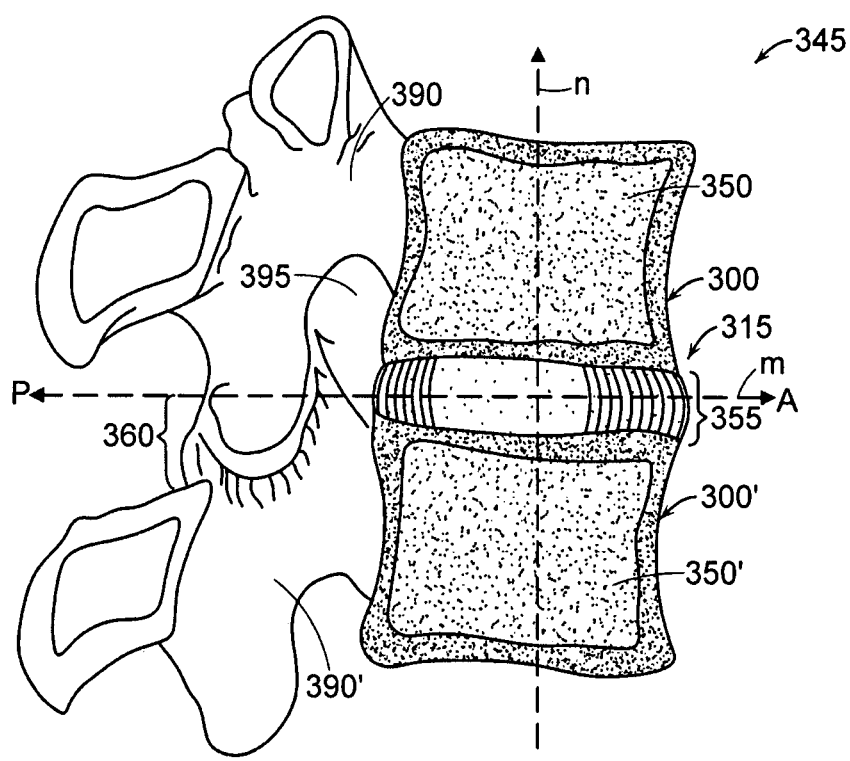
FIG. 1B is a partial cross-section, lateral view of a portion of the spine.

Referring now to FIGS. 1A and 1B which illustrate the general anatomy of a functional spine unit. In this detailed description and throughout the specification and claims, the terms "anterior", "posterior", "superior" and "inferior" are defined by their standard usage in the field of anatomy, i.e., anterior is a direction toward the front (ventral) side of the body or organ, posterior is a direction toward the back (dorsal) side of the body or organ; superior is upper (toward the head) and inferior is lower (toward the feet).

In FIG. 1A there is illustrated a cross-sectional view taken along the transverse axis "M" of vertebral body 300 with an intervertebral disc 315 positioned superior to the vertebral body 300. Axis M shows the anterior (A) and posterior (P) orientation of the functional spine unit. The intervertebral disc 315 contains the annulus fibrosus (AF) 310 which surrounds a central nucleus pulposus (NP) 320. Also shown in FIG. 1A are the left 370 and right 370' transverse spinous processes and the posterior spinous process 380.

FIG. 1B provides a sagittal section taken along sagittal axis "N" through the midline of two adjacent vertebral bodies 300 (superior) and 300' (inferior). Intervertebral disc space 355 is formed between the two vertebral bodies and contains intervertebral disc 315, which supports and cushions the vertebral bodies 300/300' and permits movement of the two vertebral bodies with respect to each other and other adjacent functional spine units.

Intervertebral disc 315 is comprised of the outer AF 310, which normally surrounds and constrains the NP 320 to be wholly within the borders of the intervertebral disc space. Axis M extends between the anterior (A) and posterior (P) of the functional spine unit 345. The vertebrae also include facet joints 360 and the superior 390 and inferior 390' pedicle that form the neural foramen 395. The facet joints and intervertebral disc translate motion and transfer load between the adjacent vertebral bodies. This complex biomechanical arrangement allows for flexion, extension, lateral bending, compression, and can withstand intense axial loading and bending cycles of around a million per year. The disc height can vary from 50% to 200% of its resting value.

Those skilled in the art will readily recognize that the functional spine unit can have a defect in the annulus, which may have been created iatrogenically, as in the performance of an anulotomy, or may be naturally occurring. Such a defect can cause degenerative disc disease and overtime will result in diminished disc height and cause further damage to the vertebral bodies and posterior elements such a the facet joints. Ultimately, this condition can result in radicular pain, sciatica, and the degeneration of adjacent vertebral segments.

Standard care for such conditions include discectomy, annular repair, nucleus augmentation, disc replacement, and fusion. Such treatments and procedures can be performed according to one or more embodiments of the present invention.

Figure 2:
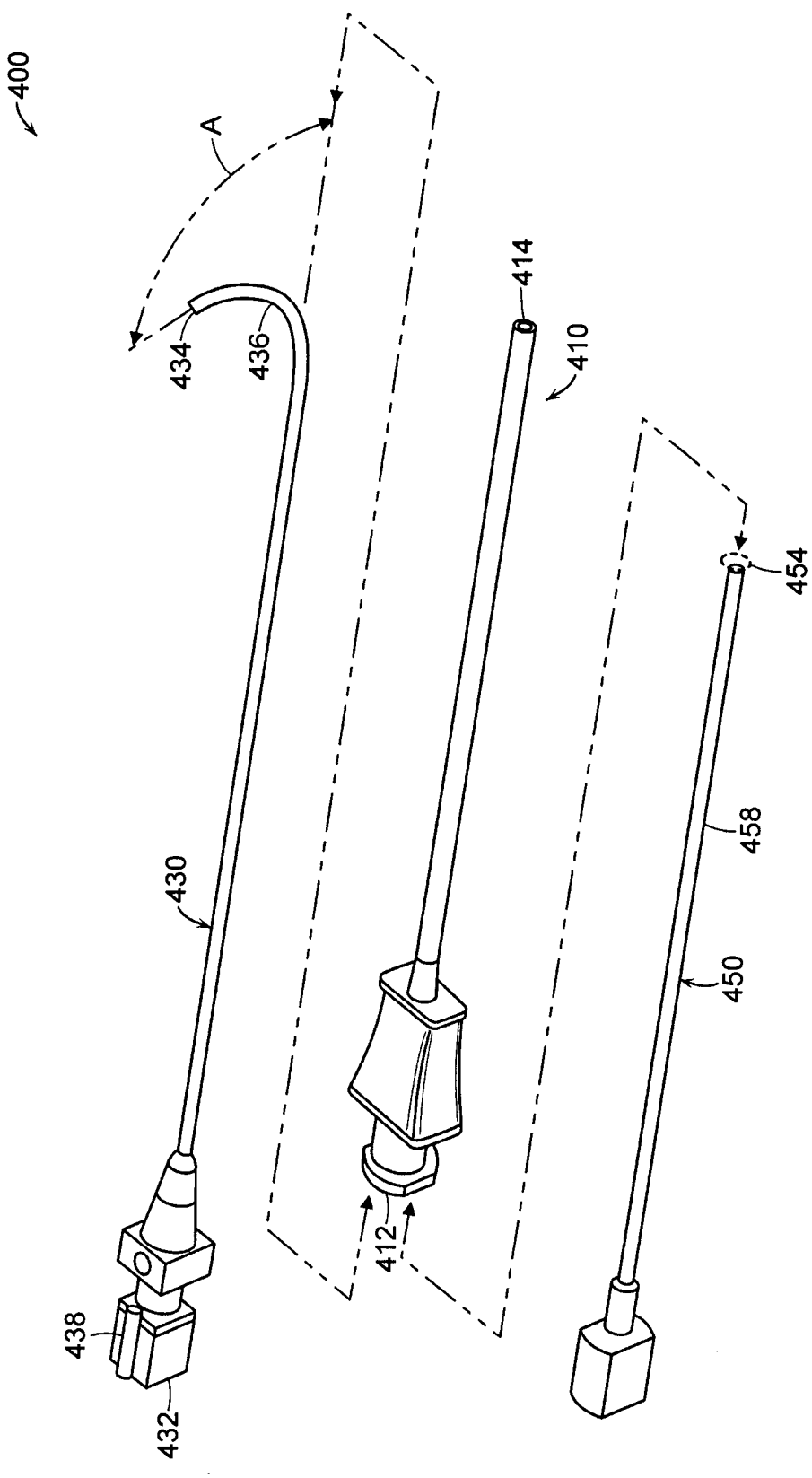
FIG. 2 is an exploded isometric view of a delivery device or a device for forming a channel in one or more vertebrae of the spine.

Referring now to FIG. 2, there is illustrated an apparatus 400 for forming a channel in a vertebral body. Apparatus 400 can also be used for delivering implants through a posterior aspect of a vertebral body such as a pedicle and placing the implant or performing a procedure proximal to the anterior aspect of the vertebral body. Apparatus 400 includes an outer cannula 410, and advancer tube 430 and a drill assembly 450. Each of the outer cannula 410, the advancer tube 430 or the drill assembly 450 can be viewed in vivo using a CT scan.

The outer cannula has a proximal end 412 and a distal end 414 and a passageway extending therebetween. The outer cannula 410 is rigid and made from material, such as, surgical steel.

The advancer tube 430 is adapted and configured for being slidably received within the passageway of the outer cannula 410 and has a central bore which extends longitudinally from a proximal end 432 of the tube to a distal end 434 of the tube. The advancer tube 430 has a preformed arcuate segment 436 when in an unconstrained configuration. The advancer tube is constrained to a second configuration when inserted into the passageway of the outer cannula 410, and wherein the advancer tube 430 returns to its unrestrained configuration when at least a portion of the tube outside the passageway of the outer cannula. U.S. Pat. No. 6,592,559 discloses techniques for forming a preformed bend or arcuate segment in shape retaining metal alloys such as Nitinol, the disclosure of which is herein incorporated by reference in its entirety.

The drill assembly 450 includes a drill bit 454 and a flexible drive cable 458. The drill bit 454 is attached to the drive cable 458 and when the drill assembly is installed the bit 454 is operatively positioned proximate to the distal end 434 of the advancer tube 430. Moreover, when the device 400 is assembled, the drive cable 458 extends from the drill bit 454 axially through the central bore of the advancer tube 430 and the drill bit 454 and the drive cable 458 are rotationally movable with respect to the advancer tube 430.

In operation, when the advancer tube 430 is moved distally with respect to the outer cannula 410 and at least a portion of the preformed arcuate segment 436 of the advancer tube 430 is in the unconstrained configuration, the drill bit 454 moves distally and traverses an arcuate path.

The advancer tube 430 is made from a shape memory alloy. In the embodiment disclosed in FIG. 2, the advancer tube 430 is made from a nickel-titanium alloy, such as nitinol. However, those skilled in the art will readily appreciate that other material can be used, such as Copper-Aluminum-Nickel, Copper-Aluminum-Zinc, Copper-Tin or Copper-Zinc or combinations thereof; or the advancer tube can be made from a plastic material.

As shown, the preformed arcuate segment 436 of the advancer tube 430 defines a bend of about 110 degrees. In certain embodiments, the preformed arcuate segment defines a bend of between about 80 and about 100 degrees. The proximal end 432 of the advancer tube 430 includes a raised surface 438 for indicating the plane of the preformed arcuate segment 436. Upon advancement of the advancer tube 430 or retraction of the outer cannula 410, the biased distal region or preformed arcuate segment 436 of the advancer tube 430 returns to its original, unconstrained shape.

Accordingly, when the outer cannula 410 is inserted perpendicularly into the spine and the arcuate segment 436 of the advancer tube 430 extends from the distal end 414 of the cannula 410 the aperture or working end in the advancer tube is positioned generally directly inferior or superior within a vertebral body. In this way tools or implants extruded from the advancer tube are directed away (or can be perpendicular) from delicate structures adjacent the spine like the aorta. Because the advancer tube is hollow other instruments may be inserted within it and directed by its bias (in any number of angles) throughout the procedure.

Figure 3:
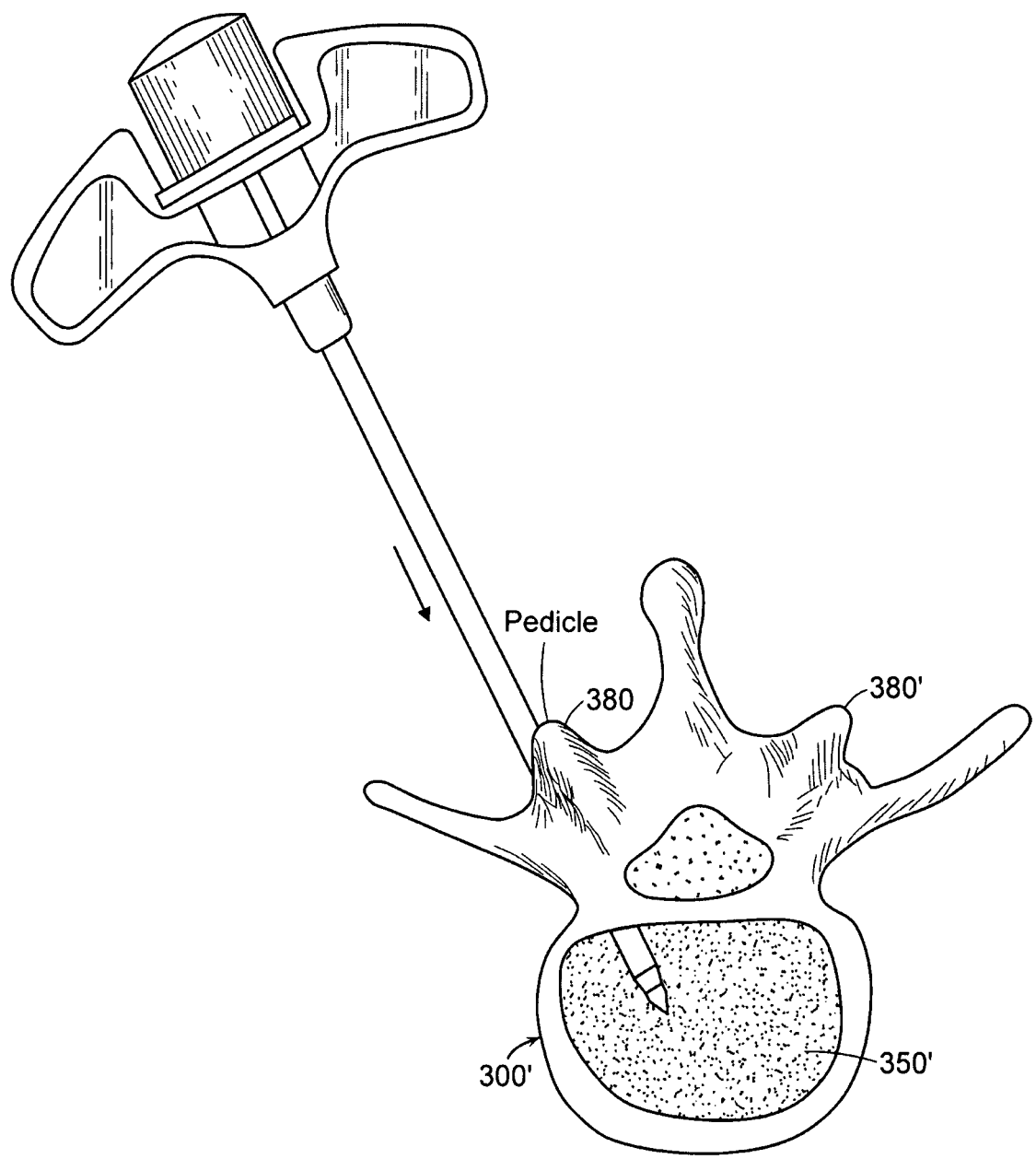
FIG. 3 provides a cross-sectional view taken horizontally through the axis of a spine and illustrating the delivery device being inserted into the vertebral body using a transpedicular approach.
Figure 4:
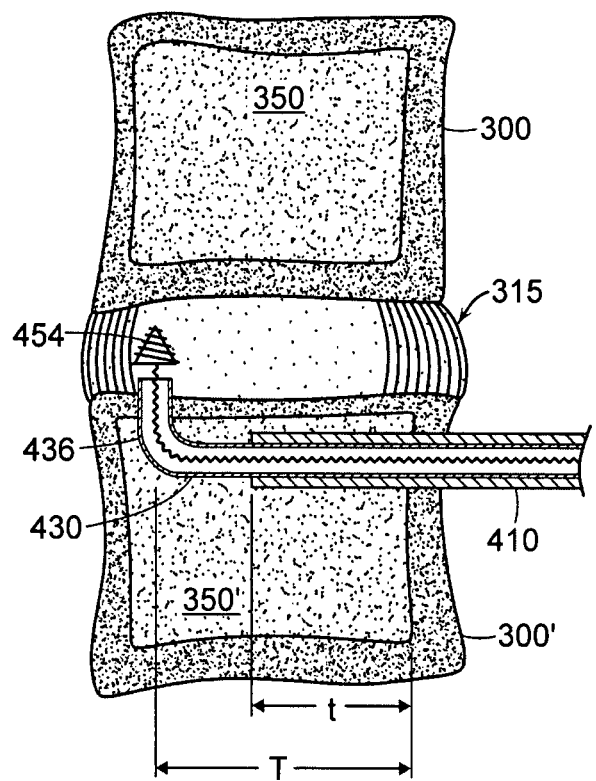
FIG. 4 is a partial cross-section, lateral view of a sagittal aspect of two adjacent vertebral bodies with a drilling assembly of the present invention shown being inserted through the side of the vertebral body and endplate of the inferior body.

As shown in FIGS. 2 through 4, a flexibly shafted drill assembly can be inserted, within the advancer tube 430. Alternatively, a debrider or forceps for removing disc tissue may also be inserted. Additional tubes or lumens may also be configured within the device to drain or deliver materials and chemicals to selected sites within the spine. Bone bags, fusion cages, spacers, one or more fusion cage elements, expanders for expanding the intervertebral space or distance between vertebral bodies may also be delivered. The lip or edge of the advancer tube 430 may also be configure with a hook, deployable anchor, or engagement surface for engaging an edge of an adjacent vertebral body (or at least a portion of the vertebral body) may also be part of the delivery device system. One or more separate engaging member may also be inserted and delivered through the tube and can be used to treat spondylolysthesis as with be discussed infra. Spondylolysthesis is a forward slipping of one vertebra over another and may result of severe instability.

One method according to the present invention is detailed in FIGS. 3 and 4. In such a representative method, open surgery is performed to the posterior portion of a selected vertebral body to expose a pedicle 380. Then, an access hole is drilled into the patient's vertebral body 300' which extends from the pedicle 380 into the marrow 350' of the vertebral body 300' to a first depth "t". Next the outer cannula 410 is inserted into the access hole up to the first depth "t" and the advancer tube 430, with or without the drill assembly operatively associated therewith, is then slidably inserted into the passageway of the outer cannula 410.

FIG. 3 shows a top view of a transverse plane through vertebral body 300' in which device 400 is inserted up to the first depth within the vertebral body. As noted above, the first depth can be predetermined or seen real time through interventional imaging e.g., CT scan, technology.

Once device 400 is positioned at the first depth, the advancer tube 430 is released from the cannula to permit the preformed arcuate segment 436 of the advancer tube to return to its unconstrained configuration and bend within the soft marrow 350'. As a result, the opening associated with the distal end 434 of the advancer tube is positioned adjacent to the vertebral endplate. Then, the flexible drilling assembly 450 is advanced through the now bent tube 430 and second access hole is drilled into the superior endplate of the vertebral body 300'. It should be noted that device 400 could simply be rotated 180 degrees to perform a similar procedure on the inferior endplate of vertebral body 300'.

FIG. 4 shows the device 400 positioned partially with vertebral body 300' and having its drill bit 454 advanced through the endplate and advanced within the intervertebral disc 315. Though shown piercing an anterior portion of the disc, the inventive method includes treating sites adjacent, along, or through the entire surface area of the vertebral endplates.

Those skilled in the art will readily appreciate that the above-described method can be performed without the use of outer cannula 410. The outer cannula 410 would not be required in applications wherein the distance "T" from the wall of the vertebral body to the location where the intervertebral disc is pierced is minimized and the preformed arcuate segment 436 of the advancer tube 430 alone will guide the drill bit 454 to the desired location.

In another embodiment access to the interior of a vertebral body can be achieved through a more lateral approach and the drill can be inserted directly into the side surface of the vertebral body. Once within the vertebral body a second access hole can be drilled into a vertebral body as described above.

According to one aspect of the invention, spondylolysthesis can be treated. First, a transpedicular access is performed followed by trans-vertebral endplate access to the intervertebral region. Then a portion of the delivery device system is used to engage the vertebral body adjacent the second access hole and a mechanical jack, piston, balloon or the like can be used to re-establish proper vertebral alignment along superior-inferior axis of the spine. For correction of spondylolysthesis along the transverse plane a second engaging member can be advanced out of the advancer tube to engage, hook onto, or otherwise serve to anchor onto the opposing vertebral endplate. Alternatively, a third access hole through the anterior annulus of the disc may be cut or drilled so that the second engaging member can hook along the edge of the adjacent vertebral body. In another embodiment the third access hole is drilled into the adjacent endplate across the disc space.

Notwithstanding the various methods and access sites for engaging the second opposing endplates the surgeon can then apply force to each vertebral body (or at least force to one vertebral body relative to the other in a push/pull dynamic) and relocate them in a proper orientation in the transverse plane. The delivery device can be configured with mechanisms to improve mechanical advantage in moving or applying force to the engaged endplates. Next the surgeon can remove the engaging members or leave them as implants. The engaging members and expansion members can be left in place or removed prior to the insertion of an intervertebral spacer, spine cage, bone bag, intermedullar rod or the like. The aforementioned implants can be delivered in one or more components or pieces or even compressed to accommodate the limiting dimensions of the delivery tubes. A hollow pedicle screw can also be implanted and serve as a guide for the delivery device and then later the hollow portion can be sealed of with a plug or threaded bolt. Finally, the method may optionally include a step utilizing bone cement, grafts, glues, and patches to fill in or close off the access holes in the vertebral bodies.

Figure 5:
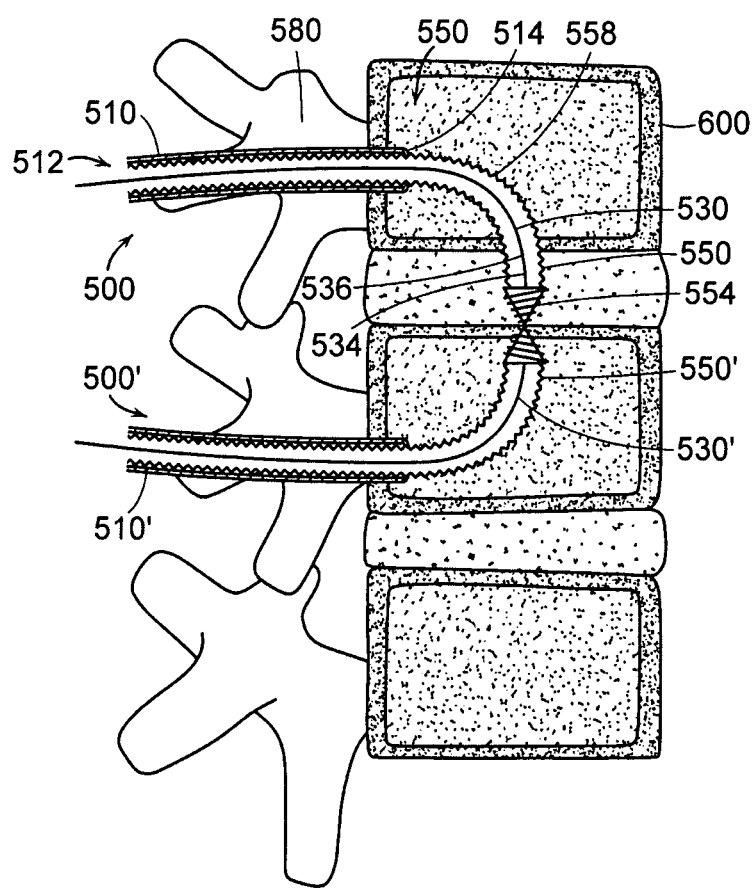
FIG. 5 is a partial cross-section, lateral view of a sagittal aspect of two adjacent vertebral bodies illustrating an alternative device and method for forming a channel in one or more a vertebral bodies.
Figure 6:
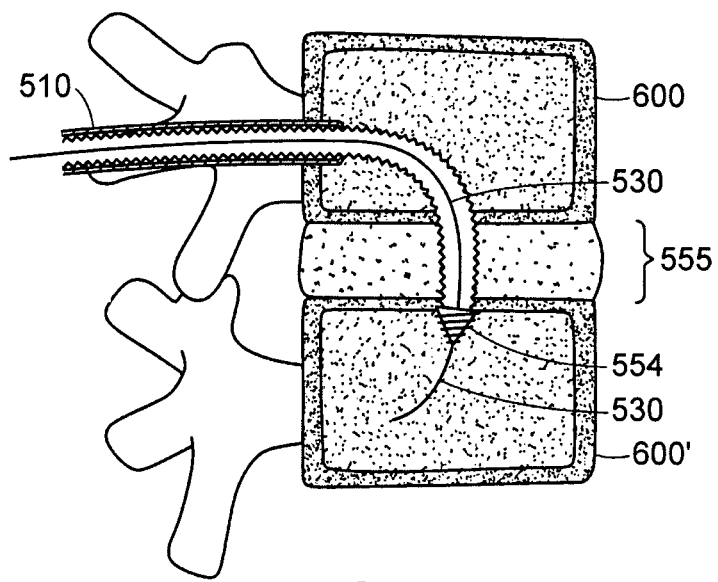
FIG. 6 is a partial cross-section, lateral view of a sagittal aspect of two adjacent vertebral bodies illustrating yet a further device and method for forming a channel in one of more vertebral bodies.

Referring now to FIGS. 5 and 6 which illustrate another device and method for forming a channel in the spine using a transpedicular approach. The device 500 includes a straight outer cannula 510, a wire 530 and a flexible drill assembly 550 or reamer. Outer cannula 510 has a proximal end 512 and a distal end 514. Wire 530 is adapted and configured for being slidably received within the central passageway of the outer cannula 510. The wire 530 has a preformed arcuate segment 536 associated with its distal end when in an unconstrained configuration. The wire 530 is constrained to a second, substantially straight configuration when inserted into the passageway of the outer cannula 510 and the wire 530 returns to its unrestrained configuration when at least a portion of the wire is outside the passageway of the outer cannula 510. Like advancer tube 430, wire 530 is made from a shape memory allow, such as nitinol. However, those skilled in the art will readily appreciate that other materials can be used, such as Copper-Aluminum-Nickel, Copper-Aluminum-Zinc, Copper-Tin or Copper-Zinc or combinations thereof, or the advancer tube can be made from a plastic material.

The drill assembly 550 includes a reamer bit 554 and a flexible drive shaft 558 which has an axial bore extending from its proximal end to its distal end. The drill assembly 550 can operates similarly to drill assembly 450, but rather than being guided by the advancer tube 430, the direction of travel of drill assembly 550 is dictated by wire 530.

In operation, when the wire 530 is moved distally with respect to the outer cannula 510 and at least a portion of the preformed arcuate segment 536 of the wire 530 is in the unconstrained configuration, the reamer bit 554 moves distally and traverses the path defined by the preformed segment 536 of the wire 530. As shown, the preformed arcuate segment 536 of the wire 530 defines a bend of about 90 degrees. Those skilled in the art will readily appreciate that the wire can be configured to have a larger or smaller bend radius in order to suit particular application. Moreover, the drill assembly can be operated manually or by a motor operatively associated with the proximal end of the flexible drive shaft 558.

A representative method for using device 500 for transpedicular access to the intervertebral disc space includes performing open or closed surgery to the posterior portion of a selected vertebral body to expose a pedicle 580. Then, an access hole is drilled into the patient's vertebral body 600 which extends from the pedicle 580 into the marrow 550' of the vertebral body 600' to a first depth. Next the outer cannula 510 is inserted into the access hole up to the first depth and the wire 530, with or without the drill assembly operatively associated therewith, is then slidably inserted into the passageway of the outer cannula 510. As noted above, the first depth can be predetermined or seen real time through interventional imaging e.g., CT scan, technology.

Once device 500 is positioned at the first depth, the wire 530 is released from the cannula to permit the preformed arcuate segment 536 to return to its unconstrained configuration and bend within the soft marrow 550'. As a result, distal end 534 of the wire is positioned adjacent to the vertebral endplate. Then, the flexible drilling assembly 550 is advanced over the now bent wire 530 and second access hole is drilled into the inferior endplate of the vertebral body 600. As shown in FIG. 6, the wire 530 could then be pushed into and across the intervertebral disc space 555 so that the drill bit can be extended to the superior endplate of the adjacent vertebral body 600'.

It should be noted that device 500 could simply be rotated 180 degrees to perform a similar procedure on the superior endplate of vertebral body 600. Moreover, opposing devices 500 and 500' can be used to create a channel that extends from one vertebral body through the intervertebral disc space to an adjacent vertebral body.

Figure 7:
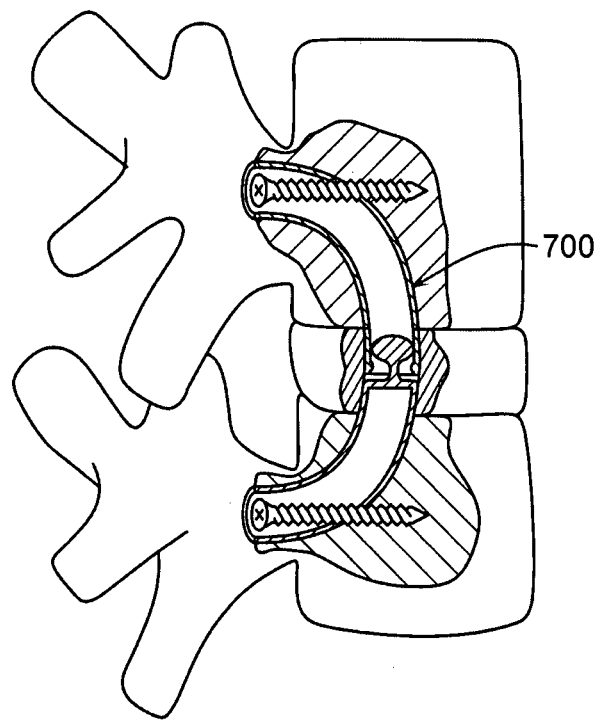
FIG. 7 is a partial cross-section, lateral view of a sagittal aspect of two adjacent vertebral bodies illustrating an implant which has been constructed in accordance with the present disclosure inserted into the channel formed in the spine.

Referring now to FIG. 7 which illustrates an implant 700 for use in a spinal stabilization procedure. Implant 700 includes a superior rod 710 and a inferior rod 720 which are inter-connected through a ball and socket joint (constrained or unconstrained). The implant 700 is shown inserted into a channel which extends from a pedicle associated with a first vertebral body, into the first vertebral body, through the intervertebral disc space and then through a second vertebral body. Moreover, bone screws are used to secure the implant 700 and prevent implant migration thereof.

Figure 8:
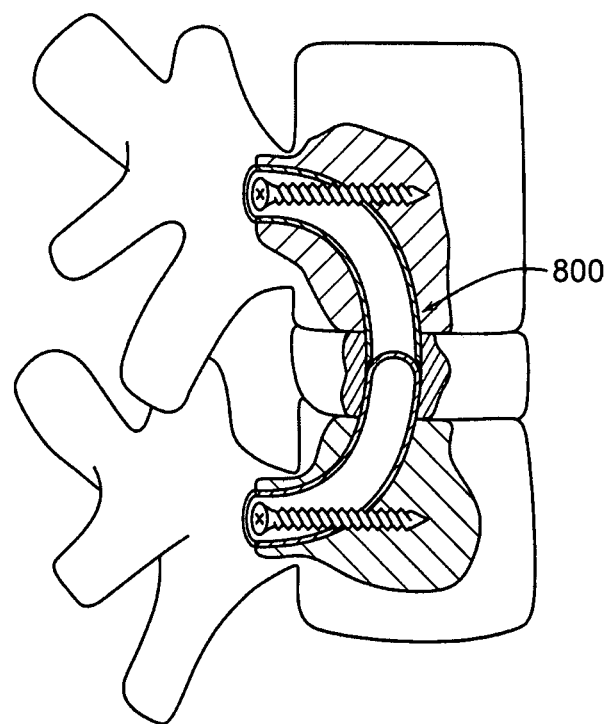
FIG. 8 is a partial cross-section, lateral view of a sagittal aspect of two adjacent vertebral bodies illustrating a second implant embodiment.
Figure 9:
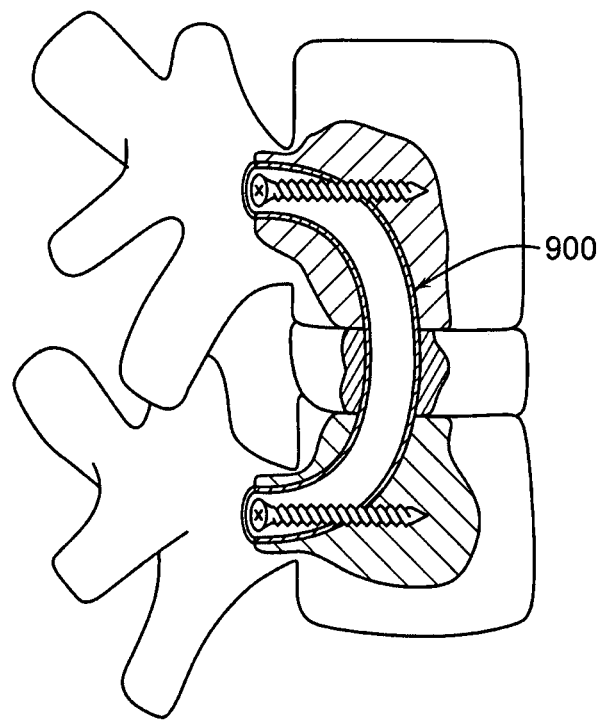
FIG. 9 is a partial cross-section, lateral view of a sagittal aspect of two adjacent vertebral bodies illustrating a third implant embodiment.

FIGS. 8 and 9 illustrate alternative implant constructions which have been designated as reference numerals 800 and 900. Implant 800 uses a different means of articulating than that of implant 700. Implant 900 is a single-piece rod which could be used in a rigid fusion. It should be noted that the implant 900 can be made from a material which is compressible so as to afford a certain amount of mobility/flexibility.

Referring now to FIGS. 10 through 12B which illustrate several new and novel bone screws which are adapted and configured for securing the implants of the present invention to the bone material and prevent implant migration. Those skilled in the art will readily appreciate that the bone screws discussed hereinbelow can be adapted for use with other implant constructions or orthopedic structures and are not limited to use with the previously described implants.

Figure 10:
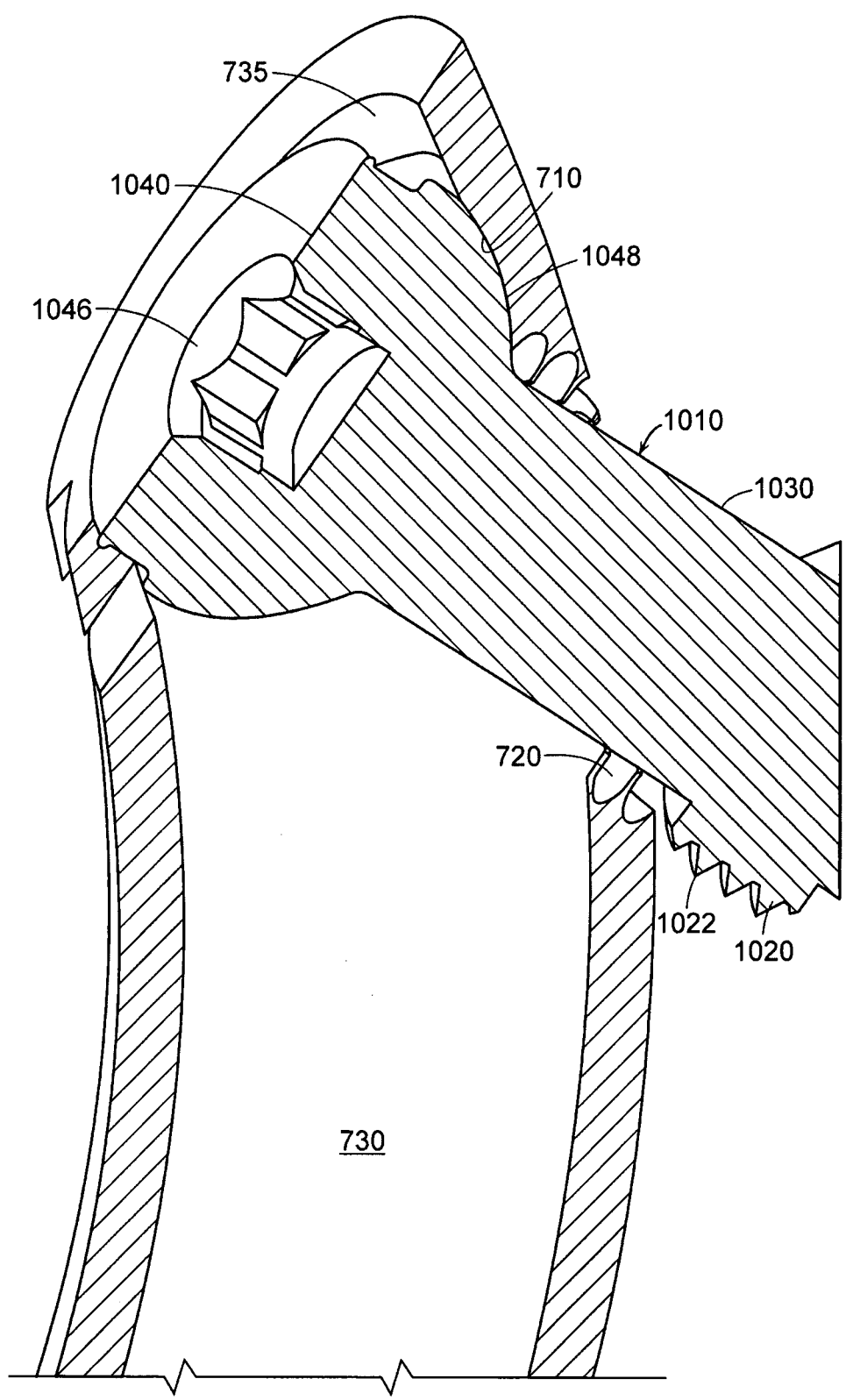
FIG. 10 provides a partial cross-sectional view of an implant for use in the presently disclosed method having a lag screw associated with an end thereof for securing the end of the implant to the bone material.

FIG. 10 details a first bone screw embodiment which has been identified by reference number 1010. Bone screw 1010 is a lag screw that has a threaded portion 1020, a neck portion 1030 and a head portion 1040. Threaded portion 1020 has a male thread series 1022 formed thereon which secures the screw 1010 to the bone material. The neck portion 1030 is cylindrical in configuration and connects the threaded portion 1020 to the head portion 1040. The implant shown in FIG. 10 can be either of the previously described implants 700, 800 or 900 or as previously mentioned, bone screw 1010 can be used with other types of orthopedic structures. Preferably, at least one end, of the implant is adapted for receiving bone screw 1010, but those skilled in the art will readily appreciate that both ends of the implant can include bone screws.

In the embodiment shown in FIG. 10, the arcuate-shaped implant has a hollow core 730 which extends along its length. The bone screw 1010 is inserted into the end 735 of the implant, through an aperture provided in the opposing wall of the implant and into the bone material. The aperture includes a female thread series 720 which corresponds to the male thread series 1022 formed on the threaded portion 1020 of the bone screw 1010. Alternatively, the aperture can be provided with a smooth inner surface having an inside diameter which is larger than the outside diameter of the thread series 1022 of the implant.

The head portion 1040 of the bone screw 1010 includes a convex lower surface 1048 and a hexagonal driving recess 1046. Bone screw 1010 can be installed by inserting a wrench into hexagonal driving recess 1046 and turning the bone screw 1010 until the convex lower surface 1048 engages with a corresponding surface 710 formed on the inner core 730 of the implant.

Figure 11A:
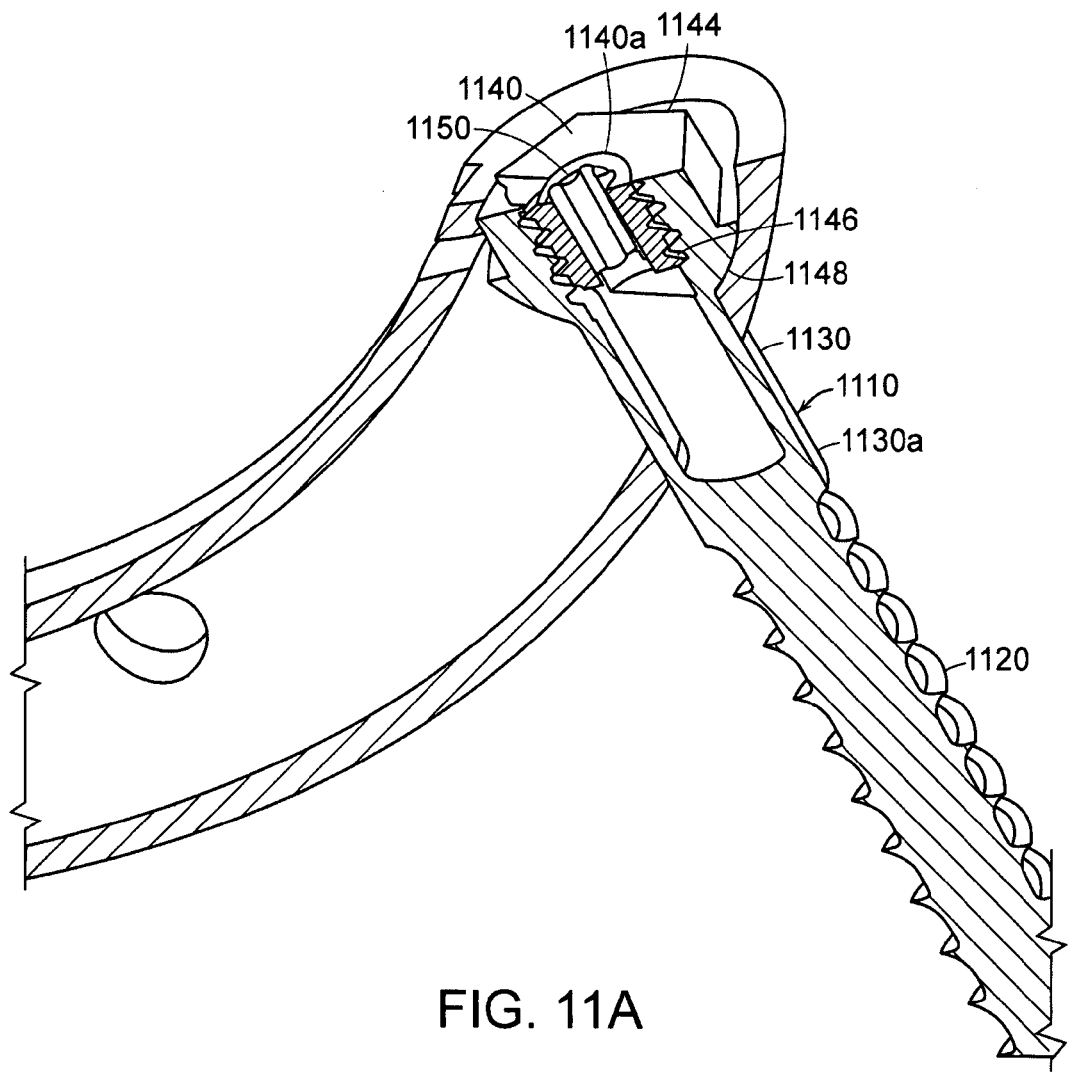
FIGS. 11A-11B provide a partial cross-sectional view of an implant embodiment of the present disclosure wherein a lag screw having a split head is used to secure the end of the implant to the bone material.
Figure 11B:
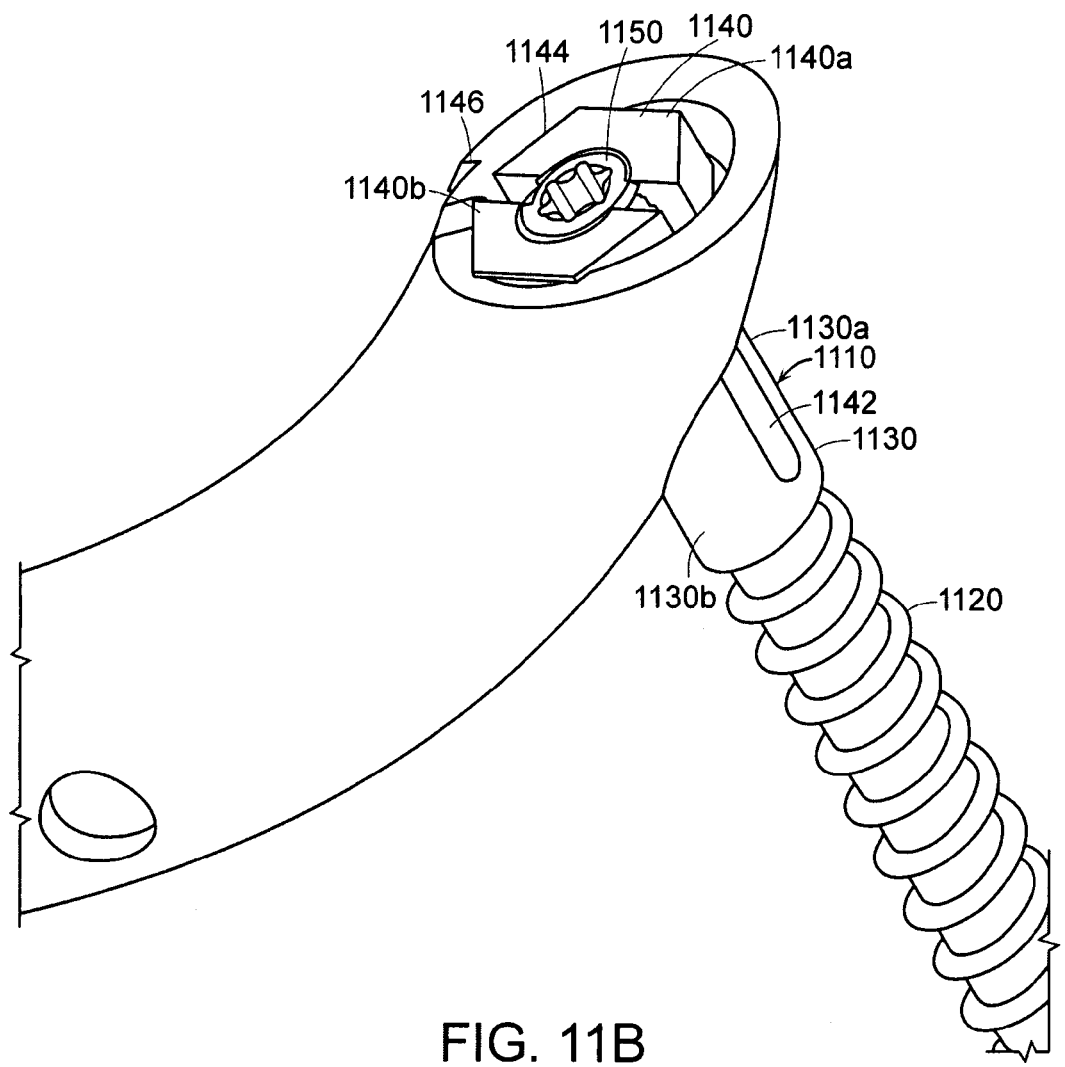

Referring now to FIGS. 11A and 11B, there is illustrated a further bone screw embodiment which has been designated by reference numeral 1110. Bone screw 1110 is similar in structure and function to screw 1010. For example, like screw 1010, bone screw 1110, includes a threaded portion 1120, a neck portion 1130 and a head portion 1140. However, unlike the screw 1010, the neck portion 1130 and head portion 1140 of screw 1110, have a longitudinal slot 1142 formed therein. Moreover, the outer perimeter 1144 of the head portion 1140 of screw 1110 is hexagonal in shape and the head portion includes a threaded recess 1146.

In operation, a wrench is used to engage the hexagonal outer perimeter 1144 of the head portion 1140 and rotate the screw 1110. Once the screw 1110 is rotated to the point that the convex lower surface 1148 of the head portion engages with a corresponding surface formed on the inner core of the implant, the wrench is removed. Then a threaded plug 1150 is screwed by wrench into the threaded recess 1146. The threaded plug 1150 is formed such that as it is screwed further into the threaded recess 1146, it forces the two opposing halves of the head portion 1140a/1140b and the neck portion 1130a/1130b apart and strengthens the connection between the implant and the screw 1110 and prevents implant migration.

Figure 12A:
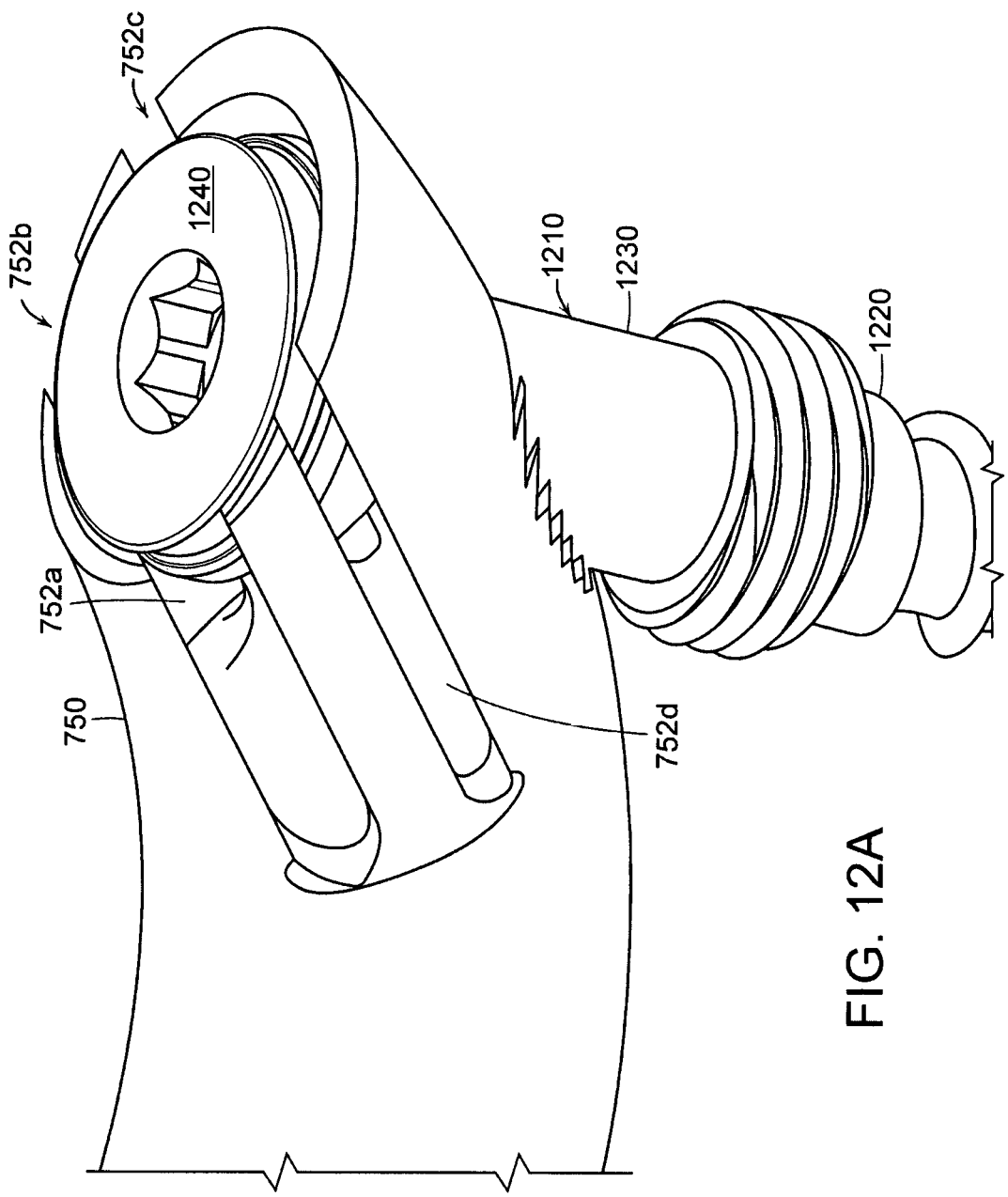
FIGS. 12A-12B provide a partial cross-sectional view of an implant embodiment of the present invention wherein the end of the implant has a series of slots formed therein.
Figure 12B:
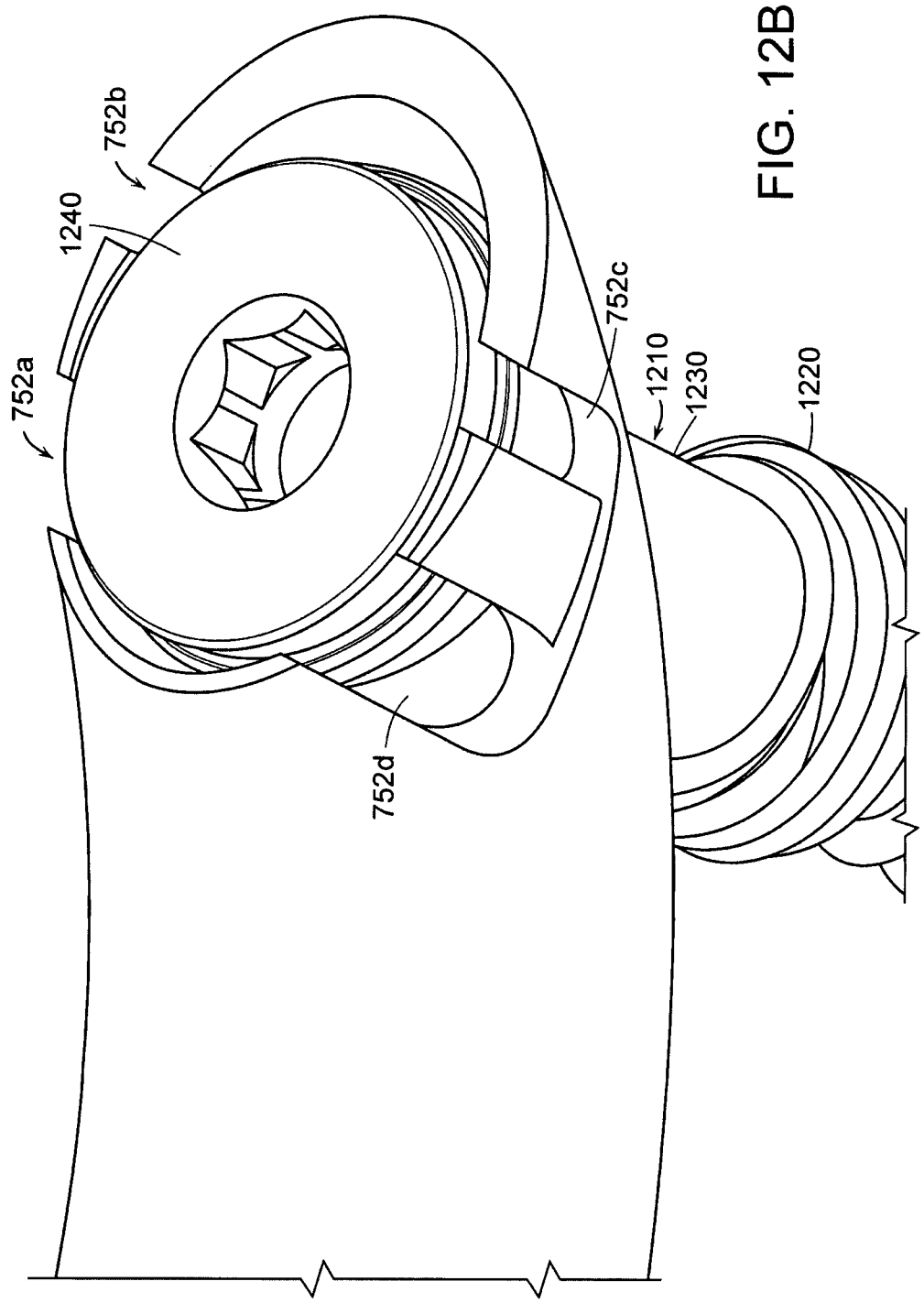

Referring now to FIGS. 12A and 12B, there is illustrated a further bone screw embodiment which has been designated by reference numeral 1210. Bone screw 1210 is also similar in structure and function to screw 1010. For example, like screw 1010, bone screw 1210, includes a threaded portion 1220, a neck portion 1230 and a head portion 1240. However, unlike the embodiment illustrated in FIG. 10, the wall 750 of the tubular implant shown in this figure includes four slots 752a-752d. Additionally, the head portion 1240 includes a convex lower surface which has a radius which does not correspond with the radius associated with the curved inner surface of the implant. Therefore, when the screw 1210 is driven into the bone material and the convex lower surface of the head portion 1240 of the screw 1210 engages with the curved inner surface of the implant, the outer wall 750 of the implant spreads apart and tulips open, increasing the frictional contact between the implant and the bone material and preventing implant migration.

Figure 13A:
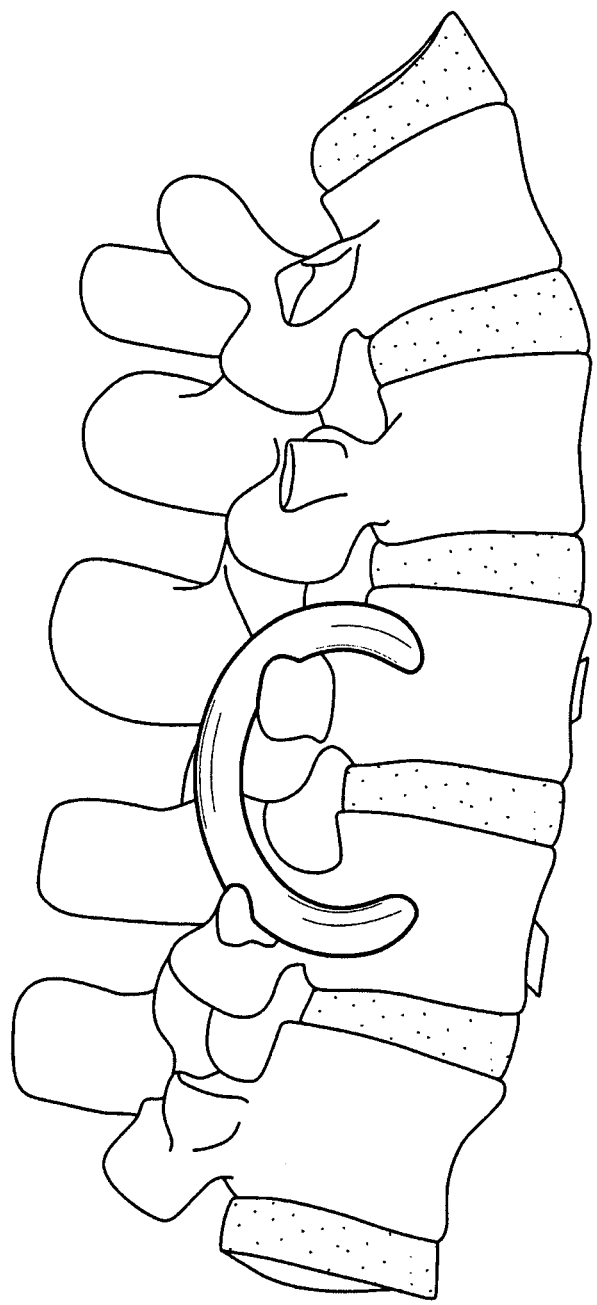
FIGS. 13A-13C provide prospective views of a spinal column and illustrate a translateral approach (red) and a transpedicular approach (green) to spinal fusion.
Figure 13B:
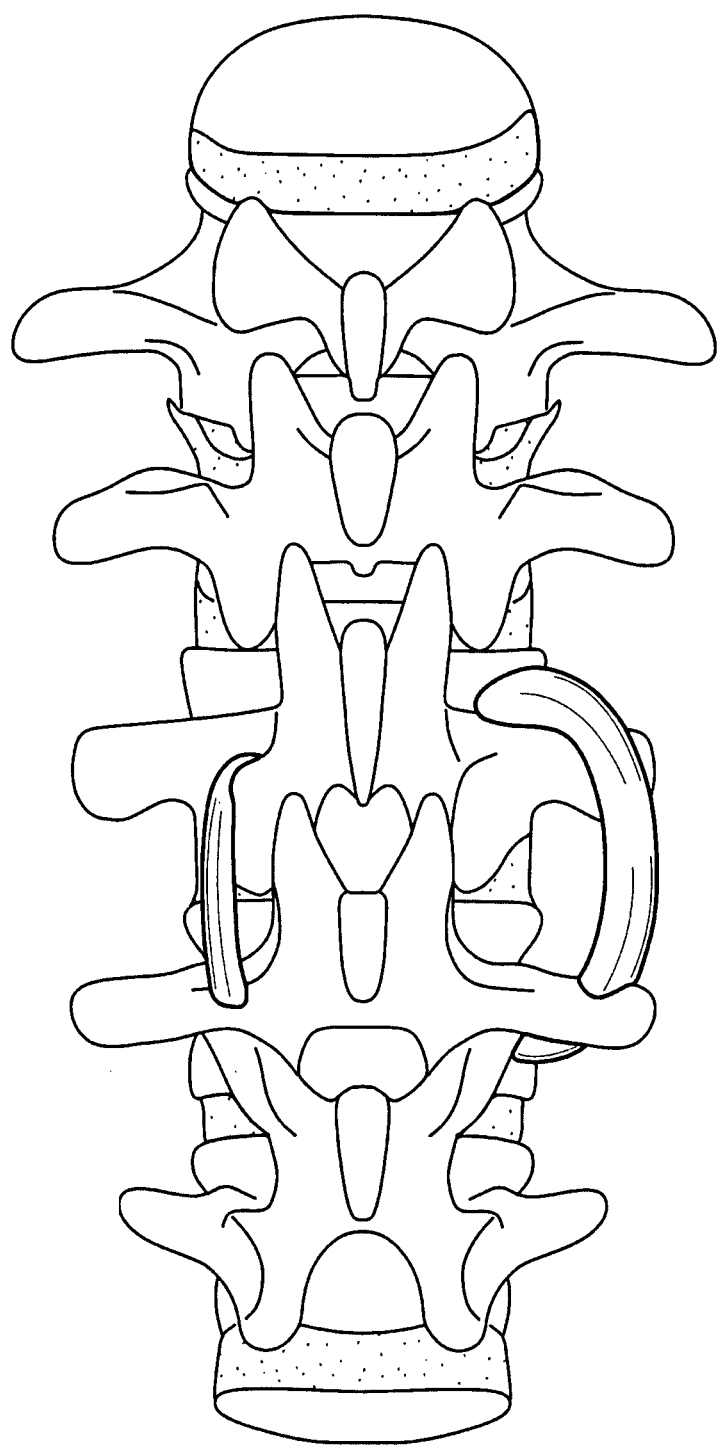
Figure 13C:
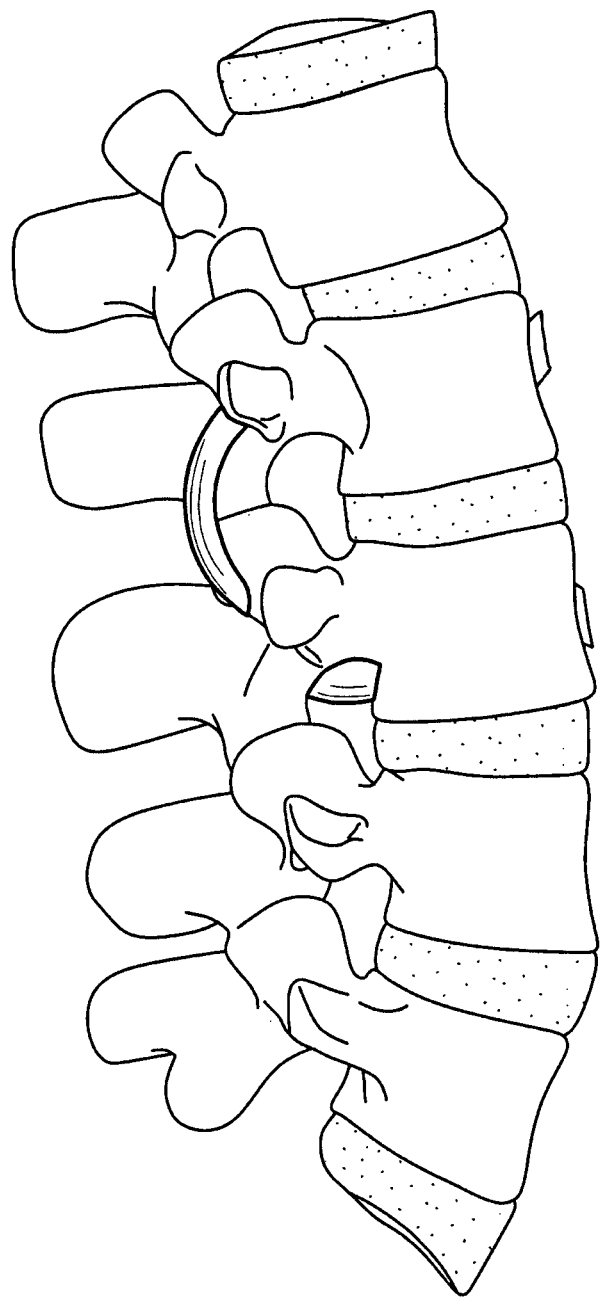

Referring now to FIGS. 13A through 13C, which provide prospective views of a spinal column and illustrate a translateral approach (red) and a transpedicular approach (green) to spinal fusion. These figures are provided in order to illustrate exemplary approaches for drilling into the spinal column and inserting implants and are not intended to limit the scope of the present disclosure.

Figure 14A:
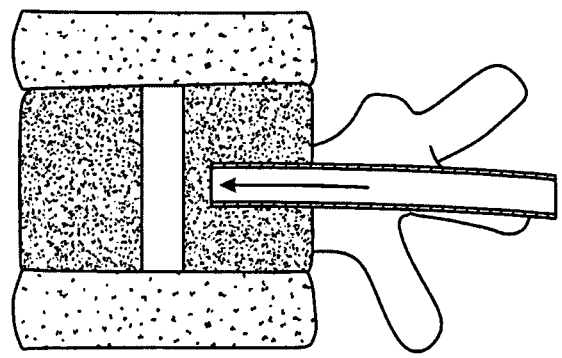
FIG. 14A is a cross-sectional view of a vertebral body having an expandable rod placed between the endplates of a vertebral body.
Figure 14B:
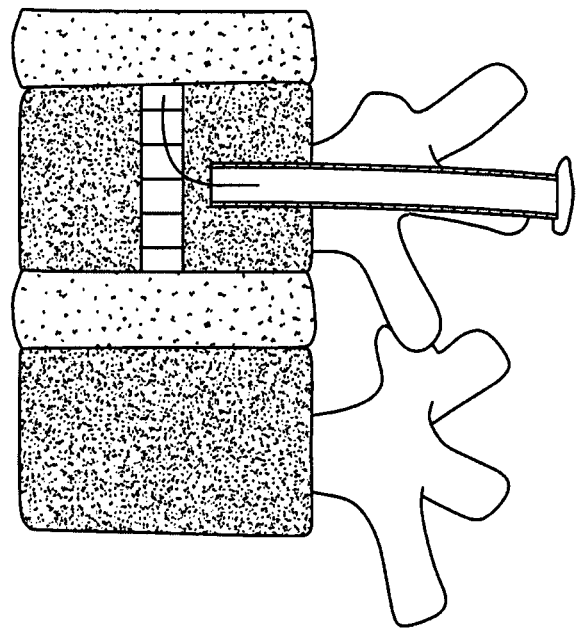
FIG. 14B is a cross-sectional view of a vertebral body having a plurality of stacked cannulas or discs positioned between the endplates of a vertebral body.

FIGS. 14A and 14B each provide a cross-sectional view of a vertebral body. In FIG. 14A, an expandable rod has been placed into the vertebral body, between the endplates in order to restore the height of a collapsed vertebral body. In FIG. 14B, a plurality of expandable/inflatable cannulas have been placed into the vertebral body, between the endplates, in order to restore the height of a collapsed vertebral body. The rod or cannulas are inserted into the vertebral body through an outer cannula or an advancer tube such as that disclosed in FIG. 2 of the present invention. In alternative embodiments, Enders rods can be placed into the vertebral body. Enders rods are curved thin rods having a diameter of between about 2 mm to 4 mm. The Enders rods can be stacked within the vertebral body so as to fill the space and act as a stabilizing device.

Those skilled in the art would readily appreciate that if spinal stabilization was achieved using transpedicular access, it would be likely that left and right implants would be used in order to provide symmetry to the support system.

Although the subject invention has been described with respect to preferred embodiments, those skilled in the art will readily appreciate that changes and modifications may be made thereto without departing from the spirit and scope of the subject invention as defined by the appended claims.

What is claimed is:

1. A method for treating a spinal region of a patient after open surgery is performed to expose a portion of the patient's spine, comprising the steps of:
    a) drilling an access hole into a first vertebral body of the patient's vertebrae which extends from a pedicle of the first vertebral body into marrow of the first vertebral body to a first depth;
    b) inserting a cannula into the access hole, the cannula having a proximal end and a distal end and a passageway extending therebetween;
    c) slidably inserting an advancer tube into the passageway of the cannula, the advancer tube having a central bore extending longitudinally from its proximal end to its distal end and having at least one preformed arcuate segment when in an unconstrained configuration, the advancer tube able to be constrained to a second configuration when inserted into the passageway of the cannula, and wherein the advancer tube returns to its unconstrained configuration when at least a portion of the tube is outside the passageway of the cannula;
    d) inserting a drill assembly into the central bore of the advancer tube, the drill assembly including a drill bit and a drive cable, the drill bit being attached to the drive cable and operatively positioned proximate to the distal end of the advancer tube, the drive cable extending from the drill bit axially through the central bore of the advancer tube, wherein the drill bit and drive cable are rotationally movable with respect to the advancer tube;
    e) sliding the advancer tube and drill bit distally with respect to the cannula to a second depth such that at least a portion of the tube is in the unconstrained configuration and the drill bit moves distally in an arcuate path through an endplate of the first vertebral body into an intervertebral disc to form an arcuate pathway;
    f) continuing the pathway through a pedicle of a second vertebral body such that the pathway is configured to receive an implant extending into the first and second vertebral bodies.

2. The method in claim 1 wherein the distal end of the advancer tube is positioned adjacent the endplate, the endplate being a superior endplate or an inferior endplate.

3. The method in claim 2 wherein a location adjacent the endplate is proximal to an anterior portion of the first vertebral body.

4. The method in claim 2 wherein a location adjacent the endplate is proximal to a medial portion of the first vertebral body.

5. The method in claim 1 wherein the access hole is through cancellous bone.

6. The method in claim 1 wherein the access hole is through cortical bone.

7. The method in claim 1 wherein the method further comprises a spinal fusion.

8. The method in claim 1 wherein the method further comprises delivering harvested bone.

9. The method in claim 1 wherein the method further comprises delivering an expansion device operable to increase a distance between adjacent endplates.

10. The method in claim 1 wherein the method further comprises at least a partial discectomy.

11. The method in claim 1 wherein the method further comprises joint motion preservation.

12. The method in claim 1 wherein the method further comprises disc repair.

13. The method in claim 1 wherein the method further comprises disc replacement.

* * * * *